(12) United States Patent
Saluja et al.

(10) Patent No.: US 8,231,861 B2
(45) Date of Patent: Jul. 31, 2012

(54) PANCREATITIS

(75) Inventors: Ashok Saluja, Golden Valley, MN (US);
Rifat Sharif, Worcester, MA (US);
Evelyn A. Kurt-Jones, Belmont, MA (US); Robert W. Finberg, Sudbury, MA (US)

(73) Assignee: University of Massachusetts, Shrewsbury, MA (US)

( * ) Notice: Subject to any disclaimer, the term of this patent is extended or adjusted under 35 U.S.C. 154(b) by 1397 days.

(21) Appl. No.: 10/579,865

(22) PCT Filed: Nov. 19, 2004

(86) PCT No.: PCT/US2004/038950
§ 371 (c)(1),
(2), (4) Date: Jun. 7, 2007

(87) PCT Pub. No.: WO2005/052192
PCT Pub. Date: Jun. 9, 2005

(65) Prior Publication Data
US 2008/0112887 A1    May 15, 2008

Related U.S. Application Data

(60) Provisional application No. 60/523,942, filed on Nov. 21, 2003.

(51) Int. Cl.
*A61K 49/00* (2006.01)
*C12Q 1/68* (2006.01)
(52) U.S. Cl. .......................................... 424/9.2; 435/6.1
(58) Field of Classification Search ........................ None
See application file for complete search history.

(56) References Cited

U.S. PATENT DOCUMENTS

| 6,740,487 B1 | 5/2004 | Schwartz et al. | |
| 2003/0125272 A1* | 7/2003 | Karras et al. | 514/44 |

FOREIGN PATENT DOCUMENTS

| WO | 03/035110 | 5/2003 |
| WO | 2004/093778 | 11/2004 |

OTHER PUBLICATIONS

Faure et al., "Bacterial lipopolysaccharide activates NF-kappaB through toll-like receptor 4 (TLR-4) in cultured human dermal endothelial cells. Differential expression of TLR-4 and TLR-2 in endothelial cells," *J. Biol. Chem.*, 275(15):11058-11063 (2000).
Genbank Acc. U88880.1:*Homo sapiens* toll-like receptor 4(TLR4) mRNA, complete cds. (1998).
Saluja and Bhagat, "Pancreatitis and associated lung injury: when MIF miffs," *Gastroenterology*, 124 (3):844-847 (2003).
Saluja and Steer, "Pathophysiology of pancreatitis. Role of cytokines and other mediators of inflammation," *Digestion*, 60(suppl.):27-33 (1999).
Singh et al., "Phosphatidylinositol 3-kinase-dependent activation of trypsinogen modulates the severity of acute pancreatitis," *J. Clin. Invest.*, 108:1387-1395 (2001).
Song et al., "Inhibition of cyclooxygenase-2 ameliorates the severity of pancreatitis and associated lung injury," *Am. J. Physiol. Gastrointest. Liv Physiol.*, 283:G1166-G1174 (2002).
Takeda et al., "Toll-like receptors," *Annu. Rev. Immunol.*, 21:335-376 (2003).
Underhill and Ozinsky, "Toll-like receptors: key mediators of microbe detection,", Curr. Op. Immunol., 14:103-110 (2002).
Vogel et al., "Cutting edge: functional characterization of the effect of the C2H/HeJ defect in mice that lack an Lpsn gene: in vivo evidence for a dominant negative mutation," *J. Immunol.*, 162(10):5666-5670 (1999).
Hatakeyama et al., "Contrasting responses of human gingival and periodontal ligament fibroblasts to bacterial cell-surface components through the CD14/Toll-like receptor system," Oral Microbiol Immunol, 18(1):14-23 (2003).
International Search Report as issued in PCT/US04/38950 on Apr. 1, 2005.
Mansell et al., "The serine protease inhibitor antithrombin III inhibits LPS-mediated NF-kappaB activation by TLR-4," FEBS Letters, 508:313-317 (2001).
Ohta et al., "Identification of a novel isoform of MD-2 that downregulates lipopolysaccharide signaling," Biochem Biophys Res Commun, 323(3):1103-1108 (2004).
Su et al., "*Helicobacter pylori* activates Toll-like receptor 4 expression in gastrointestinal epithelial cells," Infect Immun, 71(6):3496-3502 (2003).
Yoshimura et al., "Lipopolysaccharides from periodontopathic bacteria *Porphyromonas gingivalis* and *Capnocytophaga ochracea* are antagonists for human toll-like receptor 4," Infect. Immunity, 70:218-225 (2002).
Written Opinion of the International Searching Authority for PCT/US04/38950, dated Apr. 1, 2005.
International Preliminary Report on Patentability for PCT/US2004/038950, issued May 22, 2006.

* cited by examiner

*Primary Examiner* — Michael Burkhart
(74) *Attorney, Agent, or Firm* — Fish & Richardson P.C.

(57) ABSTRACT

The present invention provides methods of identifying candidate therapeutic agents for use in the treatment of acute pancreatitis.

18 Claims, 3 Drawing Sheets

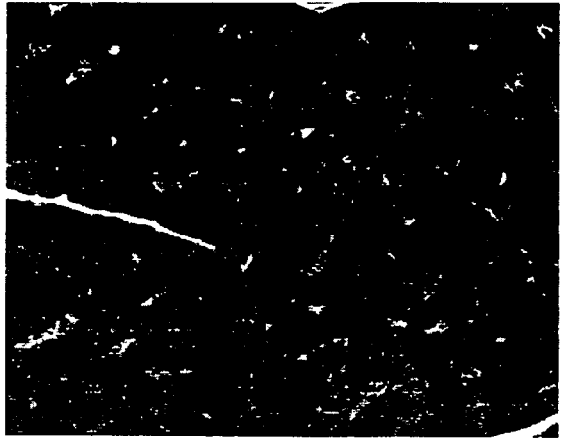
Figure 5
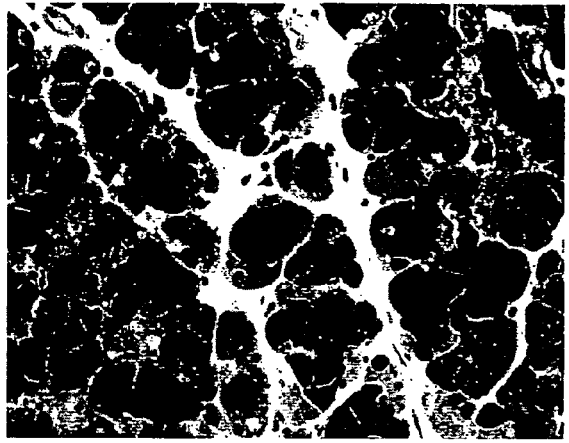
Figure 6
Figure 7
Figure 8
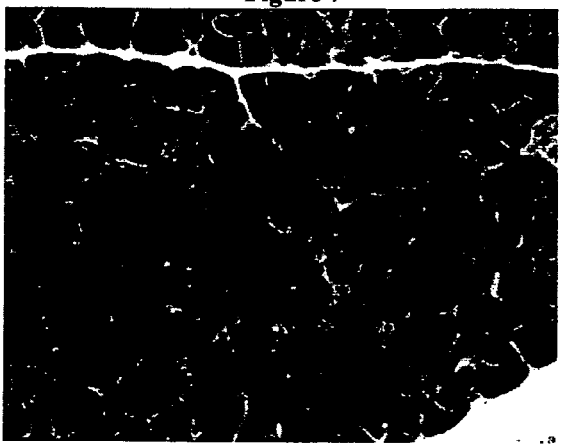
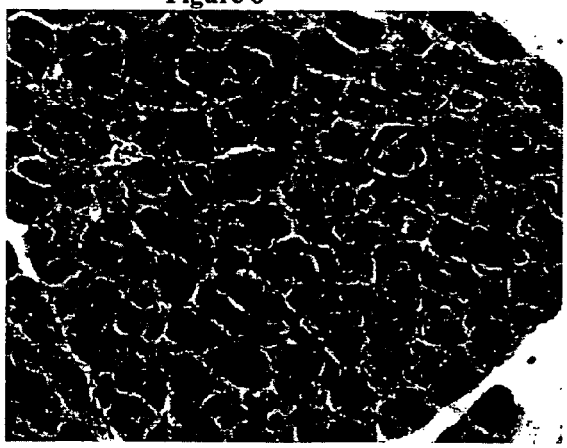
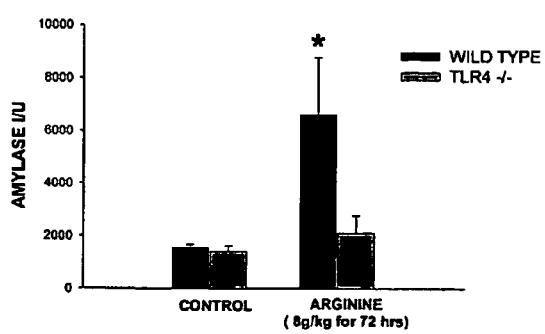
Figure 9
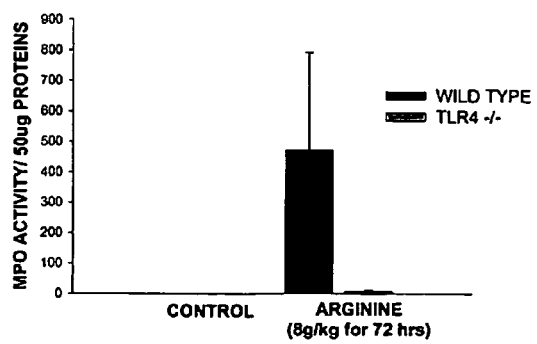
Figure 10

```
                        SEQUENCE LISTING

<160> NUMBER OF SEQ ID NOS: 53

<210> SEQ ID NO 1
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 1
ggcatttagg cagctatag                                                    19

<210> SEQ ID NO 2
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 2
gctatagctt cttcagttt                                                    19

<210> SEQ ID NO 3
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 3
ggtgtgaaat ccagacaat                                                    19

<210> SEQ ID NO 4
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 4
gccacctctc taccttaat                                                    19

<210> SEQ ID NO 5
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 5
ccattgaaga attccgatt                                                    19
```

<210> SEQ ID NO 6
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 6
attccgatta gcatactta                                              19

<210> SEQ ID NO 7
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 7
ttccgattag catacttag                                              19

<210> SEQ ID NO 8
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 8
cttagactac tacctcgat                                              19

<210> SEQ ID NO 9
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 9
ctactacctc gatgatatt                                              19

<210> SEQ ID NO 10
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 10
ctacctcgat gatattatt                                              19

<210> SEQ ID NO 11
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 11
cctcgatgat attattgac                                              19

<210> SEQ ID NO 12
<211> LENGTH: 19
<212> TYPE: DNA
<213> ORGANISM: Artificial Sequence
<220> FEATURE:
<223> OTHER INFORMATION: siRNA target sequences within human TLR4

```
<400> SEQUENCE: 12
taatttcgga tggcaacat                                                19

<210> SEQ ID NO 13
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 13
atttcggatg gcaacattt                                                19

<210> SEQ ID NO 14
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 14
tttcggatgg caacattta                                                19

<210> SEQ ID NO 15
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 15
aggcttactt tcacttcca                                                19

<210> SEQ ID NO 16
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 16
ctcagaaacc tcatttacc                                                19

<210> SEQ ID NO 17
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 17
gaaacctcat ttaccttga                                                19

<210> SEQ ID NO 18
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 18
aacctcattt accttgaca                                                19

<210> SEQ ID NO 19
<211> LENGTH: 19
<212> TYPE: DNA
```

```
<213> ORGANISM: Artificial Sequence
<220> FEATURE:
<223> OTHER INFORMATION: siRNA target sequences within human TLR4

<400> SEQUENCE: 19
tggcttgtcc agtctcgaa                                                    19

<210> SEQ ID NO 20
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 20
acagcattta actcactct                                                    19

<210> SEQ ID NO 21
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 21
tatgagccac aacaacttc                                                    19

<210> SEQ ID NO 22
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 22
gtagtctagc tttcttaaa                                                    19

<210> SEQ ID NO 23
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 23
gtttcctgca atggatcaa                                                    19

<210> SEQ ID NO 24
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 24
atgtgcaaca ccttcagat                                                    19

<210> SEQ ID NO 25
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 25
aagtatggta gaggtgaaa                                                    19
```

```
<210> SEQ ID NO 26
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 26
tgatgccttt gttatctac                                              19

<210> SEQ ID NO 27
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 27
tgcctttgtt atctactca                                              19

<210> SEQ ID NO 28
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 28
aaagccgaaa ggtgattgt                                              19

<210> SEQ ID NO 29
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 29
aagccgaaag gtgattgtt                                              19

<210> SEQ ID NO 30
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 30
agccgaaagg tgattgttg                                              19

<210> SEQ ID NO 31
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 31
gccgctggtg tatctttga                                              19

<210> SEQ ID NO 32
<211> LENGTH: 19
<212> TYPE: DNA
<213> ORGANISM: Artificial Sequence
<220> FEATURE:
<223> OTHER INFORMATION: siRNA target sequences within human TLR4
```

```
<400> SEQUENCE: 32
gcagtcgtgc tggtatcat                                                    19

<210> SEQ ID NO 33
<211> LENGTH: 19
<212> TYPE: DNA
<213> ORGANISM: Artificial Sequence
<220> FEATURE:
<223> OTHER INFORMATION: siRNA target sequences within human TLR4

<400> SEQUENCE: 33
gtcgtgctgg tatcatctt                                                    19

<210> SEQ ID NO 34
<211> LENGTH: 20
<212> TYPE: DNA
<213> ORGANISM: Artificial Sequence
<220> FEATURE:
<223> OTHER INFORMATION: synthetically generated antisense
      oligonucleotides

<400> SEQUENCE: 34
aatcccactt ccttcatgcc                                                   20

<210> SEQ ID NO 35
<211> LENGTH: 21
<212> TYPE: DNA
<213> ORGANISM: Artificial Sequence
<220> FEATURE:
<223> OTHER INFORMATION: synthetically generated antisense
      oligonucleotides

<400> SEQUENCE: 35
aatcccactt ccttcatgcc t                                                 21

<210> SEQ ID NO 36
<211> LENGTH: 19
<212> TYPE: DNA
<213> ORGANISM: Artificial Sequence
<220> FEATURE:
<223> OTHER INFORMATION: synthetically generated antisense
      oligonucleotides

<400> SEQUENCE: 36
acactgtcct cccactcca                                                    19

<210> SEQ ID NO 37
<211> LENGTH: 20
<212> TYPE: DNA
<213> ORGANISM: Artificial Sequence
<220> FEATURE:
<223> OTHER INFORMATION: synthetically generated antisense
      oligonucleotides

<400> SEQUENCE: 37
acactgtcct cccactccag                                                   20

<210> SEQ ID NO 38
<211> LENGTH: 19
<212> TYPE: DNA
<213> ORGANISM: Artificial Sequence
<220> FEATURE:
<223> OTHER INFORMATION: synthetically generated antisense
      oligonucleotides

<400> SEQUENCE: 38
agcattccca cctttgttg                                                    19
```

```
<210> SEQ ID NO 39
<211> LENGTH: 19
<212> TYPE: DNA
<213> ORGANISM: Artificial Sequence
<220> FEATURE:
<223> OTHER INFORMATION: synthetically generated antisense
      oligonucleotides

<400> SEQUENCE: 39
atcccacttc cttcatgcc                                                 19

<210> SEQ ID NO 40
<211> LENGTH: 20
<212> TYPE: DNA
<213> ORGANISM: Artificial Sequence
<220> FEATURE:
<223> OTHER INFORMATION: synthetically generated antisense
      oligonucleotides

<400> SEQUENCE: 40
atcccacttc cttcatgcct                                                20

<210> SEQ ID NO 41
<211> LENGTH: 21
<212> TYPE: DNA
<213> ORGANISM: Artificial Sequence
<220> FEATURE:
<223> OTHER INFORMATION: synthetically generated antisense
      oligonucleotides

<400> SEQUENCE: 41
atcccacttc cttcatgcct a                                              21

<210> SEQ ID NO 42
<211> LENGTH: 21
<212> TYPE: DNA
<213> ORGANISM: Artificial Sequence
<220> FEATURE:
<223> OTHER INFORMATION: synthetically generated antisense
      oligonucleotides

<400> SEQUENCE: 42
ctcttctgtg tggtttaggg c                                              21

<210> SEQ ID NO 43
<211> LENGTH: 19
<212> TYPE: DNA
<213> ORGANISM: Artificial Sequence
<220> FEATURE:
<223> OTHER INFORMATION: synthetically generated antisense
      oligonucleotides

<400> SEQUENCE: 43
gccatctgtg tctccctaa                                                 19

<210> SEQ ID NO 44
<211> LENGTH: 21
<212> TYPE: DNA
<213> ORGANISM: Artificial Sequence
<220> FEATURE:
<223> OTHER INFORMATION: synthetically generated antisense
      oligonucleotides

<400> SEQUENCE: 44
gctcttctgt gtggtttagg g                                              21
```

-continued

<210> SEQ ID NO 45
<211> LENGTH: 20
<212> TYPE: DNA
<213> ORGANISM: Artificial Sequence
<220> FEATURE:
<223> OTHER INFORMATION: synthetically generated antisense
      oligonucleotides

<400> SEQUENCE: 45
gctgcctctg gtccttgatc                                                 20

<210> SEQ ID NO 46
<211> LENGTH: 20
<212> TYPE: DNA
<213> ORGANISM: Artificial Sequence
<220> FEATURE:
<223> OTHER INFORMATION: synthetically generated antisense
      oligonucleotides

<400> SEQUENCE: 46
gggtttcatg ccagctcttc                                                 20

<210> SEQ ID NO 47
<211> LENGTH: 21
<212> TYPE: DNA
<213> ORGANISM: Artificial Sequence
<220> FEATURE:
<223> OTHER INFORMATION: synthetically generated antisense
      oligonucleotides

<400> SEQUENCE: 47
gggtttcatg ccagctcttc t                                               21

<210> SEQ ID NO 48
<211> LENGTH: 20
<212> TYPE: DNA
<213> ORGANISM: Artificial Sequence
<220> FEATURE:
<223> OTHER INFORMATION: synthetically generated antisense
      oligonucleotides

<400> SEQUENCE: 48
ggtttcatgc cagctcttct                                                 20

<210> SEQ ID NO 49
<211> LENGTH: 19
<212> TYPE: DNA
<213> ORGANISM: Artificial Sequence
<220> FEATURE:
<223> OTHER INFORMATION: synthetically generated antisense
      oligonucleotides

<400> SEQUENCE: 49
gtcttctcca ccttctgca                                                  19

<210> SEQ ID NO 50
<211> LENGTH: 19
<212> TYPE: DNA
<213> ORGANISM: Artificial Sequence
<220> FEATURE:
<223> OTHER INFORMATION: synthetically generated antisense
      oligonucleotides

<400> SEQUENCE: 50
tcccacttcc ttcatgcct                                                  19

<210> SEQ ID NO 51
<211> LENGTH: 20

```
<212> TYPE: DNA
<213> ORGANISM: Artificial Sequence
<220> FEATURE:
<223> OTHER INFORMATION: synthetically generated antisense
      oligonucleotides

<400> SEQUENCE: 51
tcccacttcc ttcatgccta                                              20

<210> SEQ ID NO 52
<211> LENGTH: 21
<212> TYPE: DNA
<213> ORGANISM: Artificial Sequence
<220> FEATURE:
<223> OTHER INFORMATION: synthetically generated antisense
      oligonucleotides

<400> SEQUENCE: 52
tcccacttcc ttcatgccta t                                            21

<210> SEQ ID NO 53
<211> LENGTH: 20
<212> TYPE: DNA
<213> ORGANISM: Artificial Sequence
<220> FEATURE:
<223> OTHER INFORMATION: synthetically generated antisense
      oligonucleotides

<400> SEQUENCE: 53
tccttaccca gtcctcatcc                                              20
```

PANCREATITIS

CLAIM OF PRIORITY

This application is the national stage of International Patent Application No. PCT/US2004/0389540, filed on 19 Nov., 2004, and claims the benefit under 35 USC §119(e) of U.S. Patent Application Ser. No. 60/523,942, filed on Nov. 21, 2003, the entire contents of which are hereby incorporated by reference.

FEDERALLY SPONSORED RESEARCH OR DEVELOPMENT

This invention was made with Government support under Grant No. DK58694 awarded by the National Institutes of Health. The U.S. Government has certain rights in this invention.

BACKGROUND

Acute pancreatitis is a multi-faceted disease that is associated with considerable morbidity and mortality. In the United States alone, more than 300,000 patients are hospitalized annually with pancreatitis. Lung, kidney, and heart failure may all occur in severe cases. Pancreatitis is a primary factor in about 3,200 deaths, and a contributing factor in about 4,000 additional deaths, annually. Direct costs attributable to pancreatitis top $2 billion annually. See, e.g., Saluja and Bhagat, Gastroenterology, 124(3):844-847 (2003).

Conventional wisdom states that pancreatitis begins with the intra-pancreatic activation of digestive enzyme zymogens, acinar cell injury, and activation of transcription factors such as Nuclear Factor Kappa B (NF-κB) and Activator Protein-1 (AP-1). This is followed by a proinflammatory cascade leading to acinar cell necrosis, systemic inflammatory response syndrome (SIRS) and distant organ dysfunction including lung injury that frequently manifests as the acute respiratory distress syndrome (ARDS). Ultimately, the severity of acute pancreatitis depends upon the extent of systemic inflammatory responses.

The Toll-Like Receptors, or "TLRs," are named for their structural and functional homology to a receptor found in the Drosophila fruit fly, named TOLL. In humans, TLRs play an important role in activating an innate immune response to pathogen-related molecules, and hence are also known as pattern recognition receptors (PRR's). Over ten members of the TLR family have been identified in the human and mouse, designated as TLR2, TLR4, TLR5, and so on, each receptor recognizing a small range of conserved molecules from a group of pathogens. TLRs are expressed on monocytes, macrophages, dendritic cells, lymphocytes and in other cell lines, including vascular endothelial cells, lung and intestinal epithelial cells, cardiac myocytes, and adipocytes.

TLR4 is perhaps the best characterized member of this family of receptors. It binds to lipopolysaccharide (LPS) as well as to a number of host protein molecules that are released at sites of damage and infection. TLR4 is a type I transmembrane protein with extracellular domains containing leucine-rich repeats that may participate in ligand recognition. The intracellular domains contain regions that are highly homologous to the intracellular domain of the IL-1R, and these regions are referred to as Toll/IL-1R (TIR) domains. The intracellular signaling pathway is known to activate mainly the NF-κB transcription factor, which, in turn, triggers the expression of many pro-inflammatory cytokines such as TNF-alpha, IL-1beta, IL-6, and IL-8, and leads to maturation of antigen-presenting cells.

SUMMARY

The present invention is based, in part, on the discovery that the Toll-Like Receptor 4 (TLR4) plays a role in the development of pancreatitis, and is therefore a target for the development of therapeutic compounds for the treatment of pancreatitis. Thus, the invention includes methods of screening for compounds that target TLR4 that are useful in the treatment of pancreatitis and pancreatitis-associated disorders such as pancreatitis-associated lung injury, heart failure, and kidney failure.

In one aspect, the new methods described herein include methods of identifying candidate therapeutic agents for use in the treatment of acute pancreatitis. The methods include providing a cell expressing a TLR4 protein; contacting the cell with a test compound; and evaluating an effect of the test compound on the activity of the TLR4 protein. A test compound that reduces the activity of the TLR4 protein is a candidate therapeutic agent for use in the treatment of acute pancreatitis, and can be selected for further evaluation, e.g., in an animal model of pancreatitis.

The test compound can be any organic or inorganic compound, including small organic or inorganic molecules, biopolymers such as nucleic acids, e.g., siRNAs or antisense nucleic acids; polypeptides such as peptides and TLR4 specific antibodies; and hybrid molecules such as ribozymes.

The test compound can reduce the activity of the TLR4 protein in a number of ways, e.g., (i) by reducing the level (number) of TLR4 proteins, i.e., by reducing the transcription of TLR4 mRNA or the half-life of TLR4 mRNA or protein, or by reducing the translation of TLR4 protein, trafficking of TLR4 protein, or cellular localization of TLR4 protein; (ii) by reducing the activity of the TLR4 protein by interfering with binding of TLR4 to a TLR4 binding partner, e.g., Toll-interacting protein (Tollip), myeloid differentiation factor 88 (MyD88), TIR domain-containing adapter protein (TIRAP/Mal), MD-2, CD14, and IL-1R-associated kinase (IRAK), or by altering one or more post-translational modifications.

In another aspect, the methods described herein include identifying candidate therapeutic agents for use in the treatment of acute pancreatitis. The methods typically include selecting a test compound identified by a method described herein as a candidate therapeutic agent; providing a model system for acute pancreatitis (e.g., an animal model, such as is known in the art and described herein); contacting the model system with the test compound; and evaluating a clinical parameter relating to the acute pancreatitis in the model system in the presence and the absence of the test compound. An improvement in the clinical parameter indicates that the test compound is a candidate therapeutic agent for use in the treatment of acute pancreatitis.

In another aspect, the new methods described herein include additional methods of identifying candidate therapeutic agents for use in the treatment of acute pancreatitis. The methods include providing a test compound that is known or suspected to decrease TLR4 activity; providing a model system for acute pancreatitis; contacting the model system with the test compound; and evaluating a clinical parameter relating to the acute pancreatitis in the model system in the presence and the absence of the test compound. An improvement in the clinical parameter indicates that the test compound is a candidate therapeutic agent for use in the treatment of acute pancreatitis.

Suitable model systems for acute pancreatitis for use in the methods described herein include animal models of acute pancreatitis, and patients diagnosed with acute pancreatitis.

In some embodiments, the parameter relating to the acute pancreatitis is evaluated by direct clinical observation, e.g., time of onset, severity, duration, or recurrence of the pancreatitis, or the occurrence, time of onset, severity, duration, or recurrence of a pancreatitis-associated disorder such as injury to one or more organ systems in the model system, e.g., lung injury, or kidney or heart failure. In some embodiments, the parameter is measured by measuring myeloperoxidase (MPO) activity, serum amylase levels, percent necrosis, or percent edema in the pancreas of the animal model.

In a further aspect, the methods described herein include a method of treating a patient (e.g., a human or veterinary patient or an experimental animal) having acute pancreatitis, by administering to the patient a therapeutically effective amount of a candidate therapeutic agent identified by a method described herein. In some embodiments the patient also has a pancreatitis-associated disorder selected from the group consisting of lung injury, kidney failure, and heart failure, and the candidate agent also treats the associated disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 5** is a photomicrograph of a section of pancreatic tissue from a wild type control (untreated) mouse, stained with hematoxylin/eosin.

FIG. 6 is a photomicrograph of a section of pancreatic tissue from a wild type mouse after 12 injections of caerulein, stained with hematoxylin/eosin.

FIG. 7 is a photomicrograph of a section of pancreatic tissue from a TLR4 knockout control (untreated) mouse, stained with hematoxylin/eosin.

FIG. 8 is a photomicrograph of a section of pancreatic tissue from a TLR4 knockout mouse after 12 injections of caerulein, stained with hematoxylin/eosin.

FIG. 9 is a bar graph illustrating the levels of serum amylase in TLR4 knockout (TLR4−/−, gray bars) and wild type mice (black bars) after administration of arginine i.p.

FIG. 10 is a bar graph illustrating the levels of myeloperoxidase (MPO) activity in TLR4 knockout (TLR4−/−, gray bars) and wild type mice (black bars) after administration of arginine i.p.

DETAILED DESCRIPTION

Figure 1:
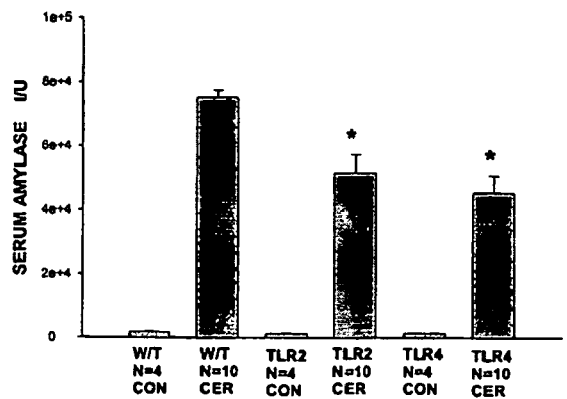
FIG. 1 is a bar graph illustrating the levels of serum amylase in TLR2 knockout (TLR2), TLR4 knockout (TLR4), and wild type (W/T) mice after twelve caerulein injections i.p. (CER).

The present invention is based, in part, on the discovery that the deletion of Toll-Like Receptor 4 (TLR4) in a knockout mouse results in significantly diminished severity of experimentally-induced pancreatitis. This is evidence that TLR4 plays a role in the development of pancreatitis, and is therefore a target for the development of therapeutic compounds for the treatment of pancreatitis.

The invention provides, inter alia, methods of screening test compounds for use as therapeutic agents to treat acute pancreatitis, and pancreatitis-associated disorders (e.g., pancreatitis-associated lung injury, heart failure, and/or kidney failure; see, e.g., Saluja and Steer, Digestion, 60(suppl. 1):27-33 (1999); Song et al., Am. J. Physiol. Gastrointest. Liver Physiol., 283:G1166-G1174 (2002); *Pancreatitis*, NIH Publication No. 03-1596, June 2003), in mammals, e.g., humans. The test compounds are evaluated for their ability to decrease the activity of TLR4, e.g., by reducing:

(a) the level (number) of TLR4 proteins; e.g., by reducing the transcription of TLR4 mRNA or the half-life of TLR4 mRNA, or by reducing the translation or half-life of the TLR4 protein, or by altering trafficking or cellular localization of TLR4 protein;

(b) the activity of the TLR4 protein directly, e.g., by interfering with binding of TLR4 to a TLR4 binding partner, e.g., Tollip, MyD88, TIRAP/MAL, MD-2, CD14, and IRAK (see, e.g., Underhill and Ozinsky, Curr. Op. Immunol., 14:103-110 (2002), or Takeda et al., Annu. Rev. Immunol., 21:335-76 (2003); and/or (c) the activity of the TLR4 protein by altering one or more post-translational modifications, or by altering trafficking or cellular localization of TLR4 protein.

Test Compounds/Candidate Therapeutic Agents

As described herein, the methods include evaluating test compounds for the ability to decrease the activity of TLR4, and, in some embodiments, further evaluating selected test compounds (e.g., candidate therapeutic agents) for use as therapeutic agents for the treatment of pancreatitis and pancreatitis-associated disorders. The test compound can be any compound, e.g., a compound that is known to have, or suspected to have, an effect on TLR4 activity, e.g., a TLR4 antagonist, or a compound of known or unknown structure in a library of compounds. In some embodiments, for example, the test compound is a biopolymer such as a nucleic acid, e.g., an siRNA, ribozyme, or antisense nucleic acid that targets a TLR4 nucleic acid; or a peptide or polypeptide, e.g., a dominant negative form of TLR4, or a TLR4 specific antibody. In some embodiments, the test compound is a small organic or inorganic molecule. In some embodiments, the test compound is subjected to one or more rounds of optimization.

Nucleic Acids

In some embodiments, the test compound comprises a nucleic acid, e.g., an siRNA, antisense or ribozyme, that targets a TLR4 sequence, e.g., the human TLR4 sequence (Genbank accession nos. U88880 and AH009665)

RNA Interference (RNAi)

RNAi is a remarkably efficient process whereby double-stranded RNA (dsRNA, also referred to herein as siRNAs or ds siRNAs, for double-stranded small interfering RNAs,) induces the sequence-specific degradation of homologous mRNA in animals and plant cells (Hutvagner and Zamore, Curr. Opin. Genet. Dev., 12:225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell., 10:549-561 (2002); Elbashir et al., Nature, 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell, 9:1327-1333 (2002); Paddison et al., Genes Dev., 16:948-958 (2002); Lee et al., Nature Biotechnol., 20:500-505 (2002); Paul et al., Nature Biotechnol., 20:505-508 (2002); Tuschl, T., Nature Biotechnol., 20:440-448 (2002); Yu et al., Proc. Natl. Acad. Sci. USA, 99(9):6047-6052 (2002); McManus et al., RNA, 8:842-850 (2002); Sui et al., Proc. Natl. Acad. Sci. USA, 99(6):5515-5520 (2002).)

One of skill in the art would readily be able to design an siRNA to disrupt TLR4 gene expression by targeting TLR4 mRNA. Thus, the test compounds can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is identical or substantially identical to the first strand. The dsRNA molecules can be chemically synthesized, or can be transcribed in vitro from a DNA template, or in vivo from, e.g., shRNA. An siRNA test compound can be, e.g., a population of identical or mixed siRNAs. The siRNAs can be designed using any method known in the art, including a number of computer-based algorithms. A number of companies provide enhanced siRNAs, e.g., Dharmacon, Inc., Lafayette, Colo. In some embodiments, the target TLR4 sequence is the open reading frame of the sequence of human TLR4 (Genbank accession no. U88880), and the siRNA is an siRNA selected from Table 1. Start refers to the starting point of the siRNA in the target TLR4 sequence (Genbank accession no. U88880).

TABLE 1

Exemplary siRNAs

| siRNA SEQUENCE | SEQ ID NO: | Start | GC Content |
|---|---|---|---|
| GGCATTTAGGCAGCTATAG | 1 | 364 | 47.37% |
| GCTATAGCTTCTTCAGTTT | 2 | 376 | 36.84% |

TABLE 1-continued

Exemplary siRNAs

| siRNA SEQUENCE | SEQ ID NO: | Start | GC Content |
|---|---|---|---|
| GGTGTGAAATCCAGACAAT | 3 | 424 | 42.11% |
| GCCACCTCTCTACCTTAAT | 4 | 469 | 47.37% |
| CCATTGAAGAATTCCGATT | 5 | 1015 | 36.84% |
| ATTCCGATTAGCATACTTA | 6 | 1025 | 31.58% |
| TTCCGATTAGCATACTTAG | 7 | 1026 | 36.84% |
| CTTAGACTACTACCTCGAT | 8 | 1040 | 42.11% |
| CTACTACCTCGATGATATT | 9 | 1046 | 36.84% |
| CTACCTCGATGATATTATT | 10 | 1049 | 31.58% |
| CCTCGATGATATTATTGAC | 11 | 1052 | 36.84% |
| TAATTTCGGATGGCAACAT | 12 | 1148 | 36.84% |
| ATTTCGGATGGCAACATTT | 13 | 1150 | 36.84% |
| TTTCGGATGGCAACATTTA | 14 | 1151 | 36.84% |
| AGGCTTACTTTCACTTCCA | 15 | 1227 | 42.11% |
| CTCAGAAACCTCATTTACC | 16 | 1500 | 42.11% |
| GAAACCTCATTTACCTTGA | 17 | 1504 | 36.84% |
| AACCTCATTTACCTTGACA | 18 | 1506 | 36.84% |
| TGGCTTGTCCAGTCTCGAA | 19 | 1568 | 52.63% |
| ACAGCATTTAACTCACTCT | 20 | 1704 | 36.84% |
| TATGAGCCACAACAACTTC | 21 | 1742 | 42.11% |
| GTAGTCTAGCTTTCTTAAA | 22 | 1870 | 31.58% |
| GTTTCCTGCAATGGATCAA | 23 | 1930 | 42.11% |
| ATGTGCAACACCTTCAGAT | 24 | 1988 | 42.11% |
| AAGTATGGTAGAGGTGAAA | 25 | 2160 | 36.84% |
| TGATGCCTTTGTTATCTAC | 26 | 2186 | 36.84% |
| TGCCTTTGTTATCTACTCA | 27 | 2189 | 36.84% |
| AAAGCCGAAAGGTGATTGT | 28 | 2350 | 42.11% |
| AAGCCGAAAGGTGATTGTT | 29 | 2351 | 42.11% |
| AGCCGAAAGGTGATTGTTG | 30 | 2352 | 47.37% |
| GCCGCTGGTGTATCTTTGA | 31 | 2395 | 52.63% |
| GCAGTCGTGCTGGTATCAT | 32 | 2446 | 52.63% |
| GTCGTGCTGGTATCATCTT | 33 | 2449 | 47.37% |

Antisense

An "antisense" nucleic acid can include a nucleotide sequence that is complementary to a "sense" nucleic acid encoding a protein, e.g., complementary to the coding strand of a double-stranded cDNA molecule or complementary to a TLR4 mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence encoding TLR4 (e.g., the 5' and 3' untranslated regions).

An antisense nucleic acid can be designed such that it is complementary to the entire coding region of a target TLR4 mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length. An antisense molecule can also be obtained commercially, e.g., using a commercial design and synthesis service such as that provided by Molecular Research Laboratories, LLC, Herndon, Va.; such services can apply proprietary or other algorithms to determine the sequence of an antisense nucleic acid to target TLR4. Antisense nucleic acids include morpholino oligos.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a TLR4 nucleic acid can be prepared, followed by testing for inhibition of TLR4 expression. Optionally, gaps of 5-10 nucleotides can be left between the oligonucleotides to reduce the number of oligonucleotides synthesized and tested. In some embodiments, the target TLR4 sequence is GenBank Accession No. U88880 and the antisense is an antisense oligo selected from Table 2.

TABLE 2

Exemplary Antisense Oligos

| Exemplary Antisense Oligo | SEQ ID NO: |
|---|---|
| 5' AATCCCACTTCCTTCATGCC 3' | 34 |
| 5' AATCCCACTTCCTTCATGCCT 3' | 35 |
| 5' ACACTGTCCTCCCACTCCA 3' | 36 |
| 5' ACACTGTCCTCCCACTCCAG 3' | 37 |
| 5' AGCATTCCCACCTTTGTTG 3' | 38 |
| 5' ATCCCACTTCCTTCATGCC 3' | 39 |
| 5' ATCCCACTTCCTTCATGCCT 3' | 40 |
| 5' ATCCCACTTCCTTCATGCCTA 3' | 41 |

TABLE 2-continued

Exemplary Antisense Oligos

| Exemplary Antisense Oligo | SEQ ID NO: |
|---|---|
| 5' CTCTTCTGTGTGGTTTAGGGC 3' | 42 |
| 5' GCCATCTGTGTCTCCCTAA 3' | 43 |
| 5' GCTCTTCTGTGTGGTTTAGGG 3' | 44 |
| 5' GCTGCCTCTGGTCCTTGATC 3' | 45 |
| 5' GGGTTTCATGCCAGCTCTTC 3' | 46 |
| 5' GGGTTTCATGCCAGCTCTTCT 3' | 47 |
| 5' GGTTTCATGCCAGCTCTTCT 3' | 48 |
| 5' GTCTTCTCCACCTTCTGCA 3' | 49 |
| 5' TCCCACTTCCTTCATGCCT 3' | 50 |
| 5' TCCCACTTCCTTCATGCCTA 3' | 51 |
| 5' TCCCACTTCCTTCATGCCTAT 3' | 52 |
| 5' TCCTTACCCAGTCCTCATCC 3' | 53 |

Antisense nucleic acid molecules for use in the methods described herein can be administered to a subject (e.g., by direct injection at a tissue site), or generated in situ such that they hybridize with or bind to cellular mRNA and/or genomic DNA encoding a TLR4 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids. Res., 15:6625-6641 (1987)). The antisense nucleic acid molecule can also comprise a 2'-o-methylribonucleotide (Inoue et al., Nucleic Acids Res., 15:6131-6148 (1987)) or a chimeric RNA-DNA analogue (Inoue et al., FEBS Lett., 215:327-330 (1987)).

TLR4 gene expression can be inhibited by targeting nucleotide sequences complementary to the regulatory region of TLR4 (e.g., promoters and/or enhancers) to form triple helical structures that prevent transcription of the TLR4 gene in target cells. See generally, Helene, Anticancer Drug Des., 6:569-84 (1991); Helene, Ann. N.Y. Acad. Sci., 660:27-36 (1992); and Maher, Bioassays, 14:807-15 (1992). The potential sequences that can be targeted for triple helix formation can be increased by creating a so-called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a TLR4-encoding nucleic acid can include one or more sequences complementary to the nucleotide sequence of a TLR4 cDNA disclosed herein, and a sequence having known catalytic sequence responsible for mRNA cleavage (see U.S. Pat. No. 5,093,246, or Haselhoff and Gerlach, Nature, 334:585-591 (1988)). For example, a derivative of a Tetrahymena L-19 IVS RNA can be constructed in which the nucleotide sequence of the active site is complementary to the nucleotide sequence to be cleaved in a TLR4-encoding mRNA. See, e.g., Cech et al., U.S. Pat. No. 4,987,071; and Cech et al., U.S. Pat. No. 5,116,742. Alternatively, TLR4 mRNA can be used to select a catalytic RNA having a specific ribonuclease activity from a pool of RNA molecules. See, e.g., Bartel and Szostak, Science, 261:1411-1418 (1993). Additional guidance on the design of antisense oligodeoxynucleotide and ribozyme molecules can be found, e.g., in Probst, Methods, 22(3):271-81 (2000). Software for predicting the secondary structure of mRNA is known in the art, see, e.g., Zuker, Nucleic Acids Res., 31(13):3406-15 (2003), and Mathews et al., J. Mol. Biol., 288:911-940 (1999). Additional information about the design and use of ribozymes can be found in Scanlon, *Therapeutic Applications of Ribozymes*, Humana Press, Totwa N.J. (1998).

Polypeptides

TLR4 Antibodies

The test compound can be an antibody that is specific for TLR4. Such antibodies can include any TLR4-specific antibody (e.g., a monospecific, or a recombinant or modified antibody), and include antigen-binding fragments thereof (e.g., Fab, F(ab')$_2$, Fv or single chain Fv fragments). The antibodies can be of the various isotypes, including: IgG (e.g., IgG$_1$, IgG$_2$, IgG$_3$, IgG$_4$), IgM, IgA$_1$, IgA$_2$, IgD, or IgE. The antibody molecules can be full-length (e.g., an IgG$_1$ or IgG$_4$ antibody) or can include only an antigen-binding fragment (e.g., a Fab, F(ab')$_2$, Fv or a single chain Fv fragment). These include monoclonal antibodies, recombinant antibodies, chimeric antibodies, humanized antibodies, deimmunized antibodies, as well as antigen-binding fragments of the foregoing.

Antibodies (e.g., monoclonal antibodies from differing organisms, e.g., rodent, sheep, human) can be produced using art-recognized methods. Once the antibodies are obtained, the variable regions can be sequenced. The location of the CDRs and framework residues can be determined (see, Kabat et al., *Sequences of Proteins of Immunological Interest*, Fifth Edition, U.S. Department of Health and Human Services, NIH Publication No. 91-3242 (1991), and Chothia et al., J. Mol. Biol., 196:901-917 (1987)). The light and heavy chain variable regions can, optionally, be ligated to corresponding constant regions. A light and the heavy immunoglobulin chains can be generated and co-expressed into the appropriate host cells.

Monoclonal anti-TLR4 antibodies can be used in the methods described herein. Suitable monoclonal antibodies can be generated using techniques known in the art. Monoclonal antibodies can be produced by a variety of techniques, including conventional monoclonal antibody methodology, e.g., the somatic cell hybridization technique of Kohler and Milstein, Nature, 256:495 (1975). See generally, Harlow and Lane, *Using Antibodies: A Laboratory Manual*, Cold Spring Harbor Laboratory Press, Cold Spring Harbor, N.Y. (1999). Although somatic cell hybridization procedures are preferred, in principle, other techniques for producing monoclonal antibodies can be employed e.g., viral or oncogenic transformation of B lymphocytes. A typical animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Useful immunogens for the purpose of this invention include peptides comprising portions of TLR4 that are unique to TLR4. Human monoclonal antibodies (mAbs) directed against human proteins can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al., International Application WO 91/00906; Kucherlapati et al., PCT publication WO 91/10741; Lonberg et al., International Application WO 92/03918; Kay et al., International Application 92/03917; Lonberg et al., Nature, 368:856-859 (1994); Green et al., Nature Genet., 7:13-21 (1994); Morrison et al., Proc. Natl. Acad. Sci. USA, 81:6851-6855 (1994); Bruggeman et al., Year Immunol., 7:33-40 (1993); Tuaillon et al., Proc. Natl. Acad. Sci. USA, 90:3720-3724 (1993); Bruggeman et al., Eur. J. Immunol., 21:1323-1326 (1991)).

TRL4 antibodies are also commercially available, e.g. from Santa Cruz Biotechnology, Inc., Santa Cruz, Calif. Monoclonal antibody MTS5510, available from Caltag Laboratories, Burlingame, Calif., is known to act as a TLR4 antagonist and can be used as such within the methods described herein.

Dominant Negatives

The test compound can also be a dominant negative form of TLR4, e.g., a peptide or polypeptide that has a mutation that adversely affects, e.g., reduces the activity of the wild-type TLR4, typically by physically combining (i.e., dimerizing) with it. For example, such dominant negative forms of TLR4 can be a truncated fragment of TLR4, e.g., a dominant negative fragment, or a missense mutation that results in dominant negative activity, e.g., as described in Faure et al., J. Biol. Chem., 275(15)11058-11063 (2000), which describes both a fragment of TLR4 that is missing the 155 C-terminal amino acids of the wild-type TLR4, and a single amino acid (P712H) mutant, both of which function as dominant negative mutants (see also, Vogel et al., J. Immunol., May 15; 162(10):5666-70 (1999). Methods of making other such mutants are known in the art, and one of skill in the art would be able to design and test such a dominant negative mutant. For example, TLR4 molecules with mutations in or deletions in a domain that interacts with a TLR4 binding partner, i.e., Tollip, MyD88, TIRAP/MAL, MD-2, CD14, and/or IRAK, may be used as dominant negatives.

Libraries

The test compound can be a molecule in a library, e.g., a library of compounds of related or unrelated structures. Such libraries are known in the art and are commercially available or can be synthesized.

Libraries of test compounds, such as small molecules, are available, e.g., commercially available, or can be synthesized using methods known in the art. As used herein, "small molecules" refers to small organic or inorganic molecules. In some embodiments, small molecules useful for the invention have a molecular weight of less than 3,000 Daltons (Da). The compounds can include organic or inorganic naturally occurring or synthetic molecules including but not limited to soluble biomolecules such as oligonucleotides, polypeptides, polysaccharides, antibodies, fatty acids, etc.

The compounds can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecule compounds are known in the art, e.g., as exemplified by Obrecht and Villalgordo, *Solid-Supported Combinatorial and Parallel Synthesis of Small-Molecular-Weight Compound Libraries* Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio., 1:60 (1997)). In addition, a number of compound, e.g., small molecule, libraries are commercially available.

Libraries and test compounds screened using the methods of the present invention can comprise a variety of types of compounds. A given library, for example, can comprise a set of structurally related or unrelated test compounds. In some embodiments, the compounds and libraries thereof can be obtained by systematically altering the structure of a first compound, e.g., a small molecule, e.g., a small molecule that is structurally similar to a known natural binding partner of TLR4 protein, or a fragment of the binding partner, or a small molecule identified as capable of binding the TLR4 protein, e.g., using methods known in the art or the methods descried herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a test compound or compounds, e.g., a small molecule. For example, in one embodiment, a general library of small molecules is screened using the methods described herein.

Optimization

Compounds identified as "hits" (e.g., compounds that decrease TLR4 activity) in the first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using the methods described herein, identifying one or more hits in that library, subjecting those hits to systematic structural alteration to create additional libraries of compounds structurally related to the hit, and screening the second library using the methods described herein.

Assays

The effect of the test compound on the activity of the TLR4 receptor can be measured using any assay known in the art. For example, the effect can be evaluated by measuring one or more of the following parameters:

(a) an effect on the level (number) of TLR4 proteins can be evaluated; e.g., by evaluating the transcription of TLR4 mRNA or the half-life of TLR4 mRNA (e.g., using a Northern blotting-based method, with or without a pulse-chase protocol to label the mRNA), or by evaluating the translation or half-life of the TLR4 protein (e.g., using a Western blotting-based method, with or without a pulse-chase protocol to label the protein), or by evaluating trafficking or cellular localization of TLR4 protein (e.g., using an imaging-based microscopy method with labeled proteins or antibodies thereto);

(b) an effect on the binding of TLR4 to a TLR4 binding partner, i.e., Tollip, MyD88, TIRAP/MAL, MD-2, CD14, and/or IRAK (e.g., using known binding assays); and/or (c) an effect on the activity of TLR4 protein by altering one or more post-translational modifications (e.g., using known assays for port-translational modifications including but not limited to glycosylation and phosphorylation).

The assay can be a high throughput assay, e.g., a high throughput assay evaluating a parameter described herein. A number of such assays, and methods for developing them, are known in the art.

In some embodiments, the method includes evaluating the effect of a test compound on one of these parameters in a first assay, selecting the "hits" from the first assay, and evaluating the test compound in a model system. For example, the model system can be an animal model of pancreatitis, and the effect of the compound can be an improvement in a clinical parameter, e.g., the clinical course of the pancreatitis (e.g., onset (i.e., delayed onset), severity (i.e., decreased severity), duration (i.e., decreased duration) and/or recurrence (i.e., decreased recurrence) of the pancreatitis). In some embodiments, the clinical parameter is evaluated in the pancreas of a model animal by measuring myeloperoxidase (MPO) activity, serum amylase levels, percent necrosis, or percent edema.

In some embodiments, the method includes providing a test compound that is known or suspected to have an effect on TLR4 activity (e.g., known to decrease TLR4 activity), and evaluating the candidate compound in a model system as described herein.

The invention is further described in the following examples, which do not limit the scope of the invention described in the claims.

EXAMPLES

Example 1

Caerulein Fails to Induce Acute Pancreatitis in TLR4 Knockout Mice

Materials

Animal models were generated as previously described (Hoshino et al., J. Immunol., 162:3749-1752 (1999)). Caerulein, a decapeptide analogue of the potent pancreatic secretagogue cholecystokinin, was purchased from Peptide International. All other chemicals and reagents were purchased from Sigma Chemical Co. (St. Louis, Mo., USA) and Diagnostic Chemicals Limited (Charlottetown, Prince Edward Island, Canada).

Animal Model of Pancreatitis

Studies were performed on wild type and TLR4−/− transgenic mice weighing about 25-30 grams. Animals were housed in cages under standard conditions at room temperature with a twelve-hour light and dark cycle. Food and drinking water were available ad libitum. Secretagogue-induced pancreatitis was elicited by the hourly (twelve times) intraperitoneal injection of caerulein (50 µg/kg). Caerulein is a specific decapeptide obtained from the skin of *Hila caerulea*, an Australian amphibian. Similar in action to cholecystokinin, caerulein stimulates gastric, biliary, and pancreatic secretion and certain smooth muscle. Clinically, caerulein is used in paralytic ileus, and as an aid in the diagnosis of pancreatic malfunction. Control animals received a comparable amount of saline. One hour after the final caerulein or saline injection, animals were sacrificed by $CO_2$ asphyxia, and tissue and blood samples were rapidly prepared for study. Harvested blood was allowed to clot and then centrifuged, and serum was obtained for measurement of amylase. The pancreas was rapidly removed and fixed in 10% neutral phosphate-buffered formalin for histological study. Other samples of pancreas were prepared for measurement of tissue myeloperoxidase (MPO) activity by snap freezing in liquid nitrogen.

Evaluation of Pancreatitis Severity

Tissue myeloperoxidase (MPO) activity was used as a marker for the sequestration of neutrophils within the pancreas by quantitating photometrically using 3,3',5,5'-tetramethylbenzidine as a substrate. Pancreatic edema was quantitated by measuring tissue water content and expressing it as a percentage of tissue wet weight. Serum amylase activity was quantitated as described in Singh et al., J. Clin. Invest., 108: 1387-1395 (2001). The extent of pancreatic acinar cell necrosis was quantitated morphometrically by an observer who was not aware of the sample identity. For these studies, paraffin-embedded samples were sectioned (5 μm) and stained with hematoxylin and eosin. Ten randomly chosen microscopic fields (×125) were examined for each tissue sample, and the extent of acinar cell injury/necrosis was expressed as a percentage of total acinar tissue.

Analysis of Data

The results reported represent mean plus or minus SE of mean values for multiple determinations from eight to ten animals (in vivo studies). The significance of changes was evaluated using student's t test when comparing two groups and ANOVA when comparing three or more groups. P values of less than 0.05 were considered to be significant.

Measurement of Pancreas Water Content

Fragments of pancreas were blotted dry and weighed to determine tissue wet weight. They were then desiccated by overnight incubation at 140° C. and reweighed to determine tissue dry weight. Tissue water content was calculated as the difference between wet and dry weight and expressed as a percentage of wet weight.

Morphological Examination

Paraffin-embedded pancreas samples were sectioned (5 μm), stained with hematoxylin/eosin, and examined by an experienced morphologist who was not aware of the sample identity. Acinar-cell injury/necrosis was quantitated by morphometry as described. For these studies, 10 randomly chosen microscopic fields (×125) were examined for each tissue sample and the extent of acinar-cell injury/necrosis was expressed as the percent of the total acinar tissue that was occupied by areas meeting the criteria for injury/necrosis. Those criteria were defined as vacuolization and swelling of acinar cells and the destruction of the histoarchitecture of whole or parts of the acini, both of which had to be associated with an inflammatory reaction. Lung tissues can be evaluated using similar methodology.

Serum Amylase Activity and Myeloperoxidase (MPO) Assays

Serum amylase activity was measured with α-amylase (Diagnostic Chemicals Limited, Canada) as a substrate on Cobas FARA Autoanalyzer. Neutrophil sequestration in the pancreas was quantitated by measuring tissue MPO activity. For these measurements, tissue samples harvested at the time of sacrifice were stored at −70° C. They were thawed, homogenized with Teflon homogenizer in 1 ml of 50 mM phosphate buffer (pH 7.4), centrifuged (14,000×g, 15 minutes, 4° C.) and the resulting pellet was resuspended in 50 mM phosphate buffer (pH 7.4) and centrifuged (14,000×g, 15 minutes, 4° C.) again.

The pellet thus obtained was resuspended in 50 mM phosphate buffer 50 mM (pH 6.0) containing 0.5% hexadecyltrimethylammonium bromide (Sigma) and homogenized with a Polytron® homogenizer. The suspension was subjected to one cycle of freeze (−80° C.) and thaw (37° C.) and further disrupted by sonication (40 seconds). The sample was then centrifuged (14,000×g, 15 minutes, 37° C.) and the supernatant were used for the MPO assay. The reaction mixture consisted of this extracted enzyme, 20 mM tetramethylbenzidine (Sigma), 100 mM sodium phosphate buffer (pH 5.4), 0.5% hexadecyltrimethylammonium bromide (Sigma) and 0.03% hydrogen peroxide. This mixture was incubated at 37° C. for 200 seconds and the increase in absorbance at 655 nm was measured in a Cobas FARA autoanalyzer.

Results

Wild-type mice given i.p. injections of a supramaximally stimulating dose of the secretagogue caerulein develop acute edematous pancreatitis. This is manifested by a rise in serum amylase activity, pancreatic MPO activity (an indicator of neutrophils sequestration in the pancreas), and morphological evidence of extensive acinar cell necrosis (FIG. 6). In contrast, caerulein administration to TLR4−/− mice resulted in significantly less severe pancreatitis (FIG. 8).

Figure 2:
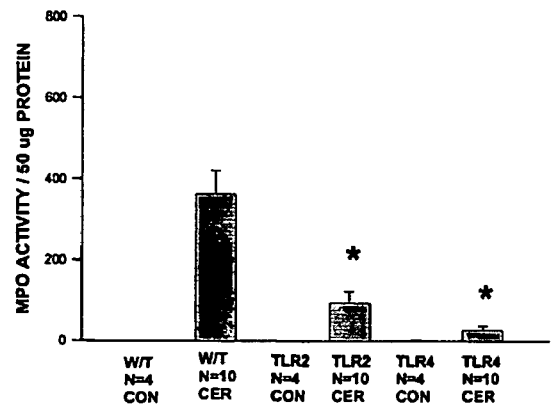
FIG. 2 is a bar graph illustrating myeloperoxidase (MPO) activity in TLR2 knockout (TLR2), TLR4 knockout (TLR4), and wild type (W/T) mice after twelve caerulein injections i.p. (CER).
Figure 3:
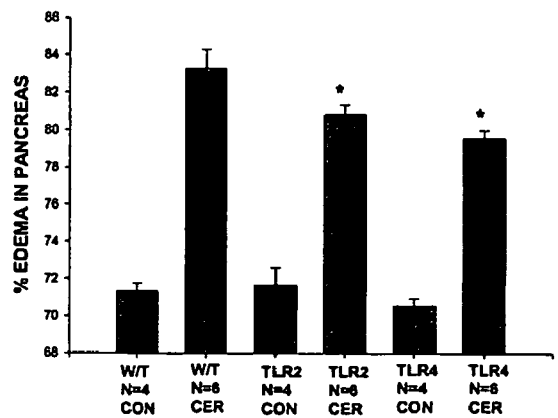
FIG. 3 is a bar graph illustrating the percent edema in the pancreas of TLR2 knockout (TLR2), TLR4 knockout (TLR4), and wild type (W/T) mice after twelve caerulein injections i.p. (CER).
Figure 4:
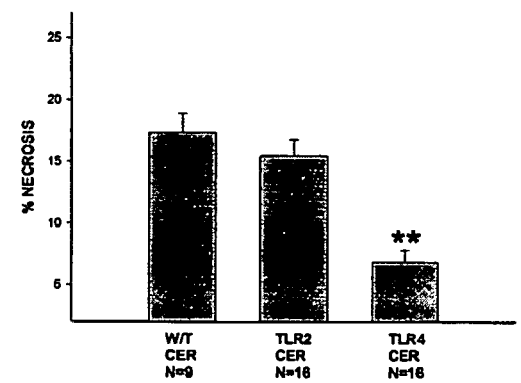
FIG. 4 is a bar graph illustrating the percent necrosis in the pancreas of TLR2 knockout (TLR2), TLR4 knockout (TLR4), and wild type (W/T) mice after twelve caerulein injections i.p. (CER).  p value <0.01 W/T vs TLR4 knockout

As can be seen in FIG. 1, serum amylase activity was reduced more than 1.6 fold in TLR4−/− mice as compared to wild type mice. In addition, MPO activity was significantly reduced from 363.30±58.54 in wild type to 88.00±9.75 in TLR4−/− mice pancreas (FIG. 2). Similarly, pancreatic water content was reduced from 83.30±0.41 in wild type to 79.56±0.43 in TLR4−/− mice after 12 caerulein i.p. injections (FIG. 3). Acinar cell necrosis in the pancreas of TLR4−/− mice (as shown in FIG. 4) after caerulein administration for 12 hours was significantly reduced to 6.83±0.98 as compared to 17.38±1.50 in wild type mice.

Histology of Secretagogue-Induced Pancreatitis

Marked inflammation and acinar cell necrosis, clearly apparent in the caerulein treated wild type mouse pancreas (FIG. 6; compare to untreated control mouse, FIG. 5), is decreased in the TLR4−/− mouse pancreatic tissue (FIG. 8; compare to untreated control knockout mouse, FIG. 7).

These results indicate that TLR4 plays a role in the development of pancreatitis.

Example 2

Arginine Fails to Induce Acute Pancreatitis in TLR4 Knockout Mice

To evaluate the effect of the absence of TLR4 in another model of pancreatitis, a new mouse model was created. Excessive doses of arginine has been shown to induce acute necrotizing pancreatitis in rats. See, e.g., Tani et al., Dig. Dis. Sci. 35, 367-374 (1990).

Briefly, pancreatitis was induced in wild type and TLR-4 knock out mice by injecting (i.p.) arginine at a dose of 800 mg/100 g body weight. This dose of arginine was divided in two parts, one half injected at the beginning of the experiment and the other half injected one hour later. Three days later mice were sacrificed and the parameters relating to the severity of pancreatitis were evaluated. Analysis was performed substantially as described above.

Results. Administration of arginine to normal mice resulted in pancreatitis that was more severe than that observed with caerulein administration. Furthermore, administration of similar doses of arginine to TLR4 knock out mice resulted in significantly milder pancreatitis compared to that observed in wild type mice. As can be seen in FIG. 9, serum amylase activity was reduced more than 2.5 fold in TLR4−/− mice as compared to wild type mice. In addition, MPO activity was significantly reduced from 472±320 in wild type to 6.8±6.2 in TLR4−/− mice pancreas (FIG. 10).

Histology of Arginine-Induced Pancreatitis

Figure 11:
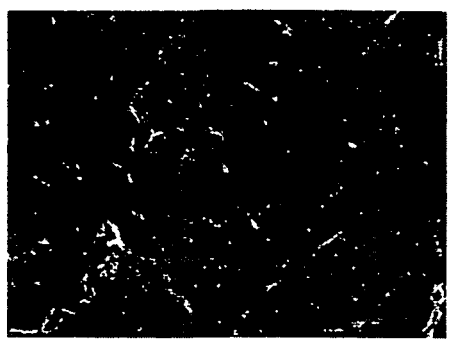
FIG. 11 is a photomicrograph of a section of pancreatic tissue from a wild type control (untreated) mouse, stained with hematoxylin/eosin.
Figure 12:
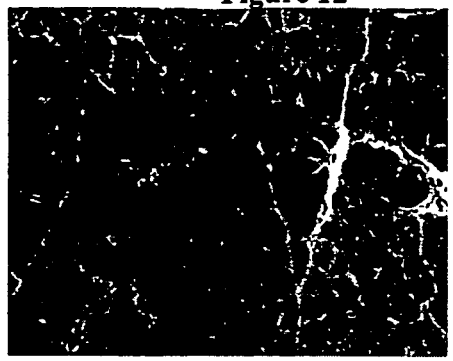
FIG. 12 is a photomicrograph of a section of pancreatic tissue from a TLR4 knockout control (untreated) mouse, stained with hematoxylin/eosin.
Figure 13:
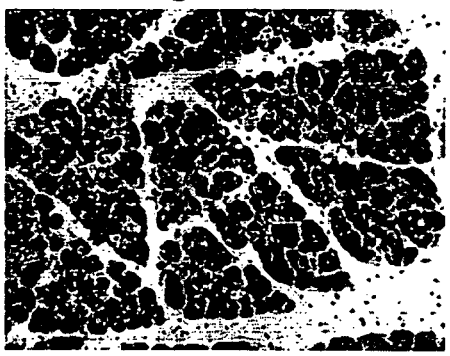
FIGS. 13, 15 and 17 are photomicrographs of sections of pancreatic tissue from a wild type mouse after administration of arginine, stained with hematoxylin/eosin, at 10× (FIG. 13), 20× (FIG. 15), and 40× (FIG. 17) magnification.
Figure 14:
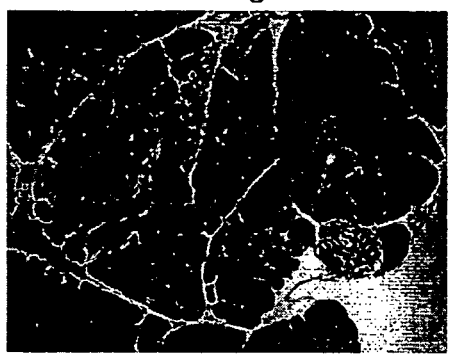
FIGS. 14, 16 and 18 are photomicrographs of sections of pancreatic tissue from a TLR4 knockout mouse after administration of arginine, stained with hematoxylin/eosin, at 10× (FIG. 14), 20× (FIG. 16), and 40× (FIG. 18) magnification.
Figure 15:
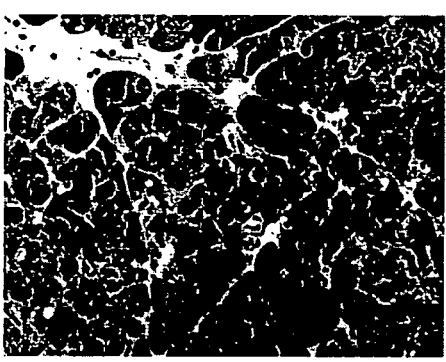
Figure 16:
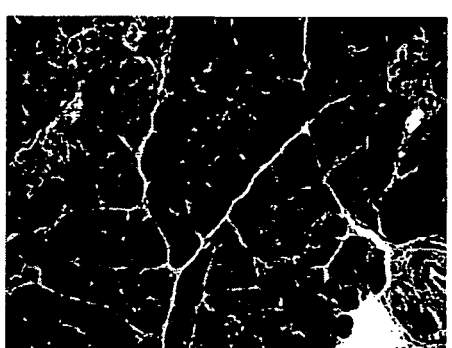
Figure 17:
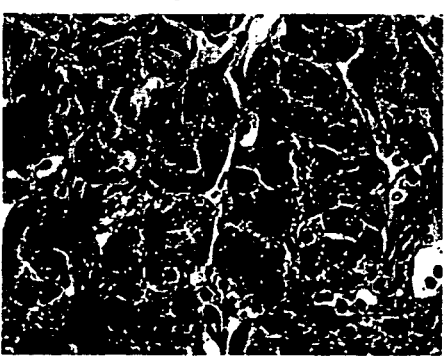
Figure 18:
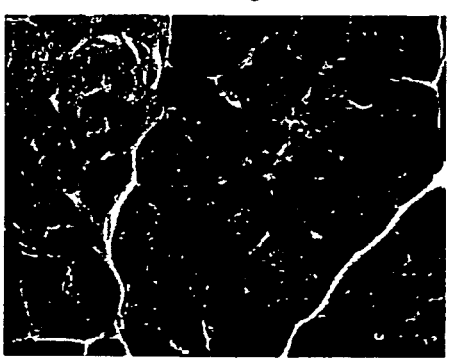

Marked inflammation and acinar cell necrosis, clearly apparent in the arginine treated wild type mouse pancreas (FIGS. 13 (10×), 15 (20×) and 17 (40×); compare to untreated control mouse, FIG. 11), is decreased in the TLR4−/− mouse pancreatic tissue (FIGS. 14 (10×), 16 (20×) and 16 (40×); compare to untreated control knockout mouse, FIG. 12).

These results, like those obtained with the secretagogue-induced model of pancreatitis described in Example 1, indicate that TLR-4 plays a significant pro-inflammatory role in pancreatitis, and inhibition of TLR-4 activation decreases the severity of pancreatitis.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a candidate therapeutic agent for use in the treatment of acute pancreatitis, the method comprising:
   providing a cell expressing a TLR4 protein;
   contacting the cell with a test compound;
   performing an assay to measure an activity of the TLR4 protein in the presence of the test compound, and
   selecting the test compound as a candidate agent for treating acute pancreatitis if the compound reduces the activity of the TLR4 protein.

2. The method of claim 1, wherein the test compound reduces the activity of the TLR4 protein by reducing a level of TLR4 proteins.

3. The method of claim 2, wherein the test compound reduces the level of TLR4 proteins by reducing one or more of (i) transcription of TLR4 mRNA or (ii) half-life of TLR4 mRNA.

4. The method of claim 2, wherein the test compound reduces the level of TLR4 proteins by reducing one or more of (i) translation of TLR4 protein, (ii) trafficking of TLR4 protein, (iii) half-life of TLR4 protein, or (iv) cellular localization of TLR4 protein.

5. The method of claim 1, wherein the test compound reduces the activity of the TLR4 protein by interfering with binding of TLR4 to a TLR4 binding partner.

6. The method of claim 5, wherein the TLR4 binding partner is selected from the group consisting of Toll-interacting protein (Tollip), myeloid differentiation factor 88 (MyD88), TIR domain-containing adapter protein (TIRAP/MAL), MD-2, CD14, and IL-1R-associated kinase (IRAK).

7. The method of claim 1, wherein the test compound reduces the activity of the TLR4 protein by altering one or more post-translational modifications.

8. The method of claim 1, wherein the test compound is an siRNA.

9. The method of claim 1, further comprising:
   providing a model system for acute pancreatitis;
   contacting the model system with a test compound that reduces an activity of the TLR4 protein; and
   evaluating a clinical parameter relating to the acute pancreatitis in the model system in the presence and the absence of the test compound,
   wherein an improvement in the clinical parameter indicates that the test compound is a candidate therapeutic agent for use in the treatment of acute pancreatitis.

10. The method of claim 9, wherein the model system is an animal model of acute pancreatitis.

11. The method of claim 10, wherein the parameter is measured by measuring myeloperoxidase (MPO) activity, serum amylase levels, percent necrosis, or percent edema in the pancreas of the animal model.

12. The method of claim 9, wherein the model system is a patient diagnosed with acute pancreatitis.

13. The method of claim 9, wherein the parameter relating to the acute pancreatitis is time of onset, severity, duration, or recurrence.

14. The method of claim 9, wherein the parameter relating to the acute pancreatitis is the presence of a pancreatitis-associated disorder selected from the group consisting of lung injury, kidney failure, and heart failure.

15. The method of claim 1, wherein the test compound is a small molecule.

16. The method of claim 1, wherein the test compound is an antisense nucleic acid.

17. The method of claim 1, wherein the test compound is a ribozyme.

18. The method of claim 1, wherein the test compound is a TLR4-specific antibody.

* * * * *

UNITED STATES PATENT AND TRADEMARK OFFICE
CERTIFICATE OF CORRECTION

| | | |
|---|---|---|
| PATENT NO. | : 8,231,861 B2 | Page 1 of 1 |
| APPLICATION NO. | : 10/579865 | |
| DATED | : July 31, 2012 | |
| INVENTOR(S) | : Ashok Saluja et al. | |

It is certified that error appears in the above-identified patent and that said Letters Patent is hereby corrected as shown below:

On the first page, Column 2 (Other Publications), Line 21, delete "C2H/HeJ" and insert -- C3H/HeJ --

In Column 1, Line 6, delete "PCT/US2004/0389540," and insert -- PCT/US2004/038950, --

In Column 1, Line 7, delete "Nov.," and insert -- Nov. --

Signed and Sealed this
Fifteenth Day of January, 2013

David J. Kappos
*Director of the United States Patent and Trademark Office*